US 6,274,174 B1

(12) United States Patent
Hom-ma et al.

(10) Patent No.: US 6,274,174 B1
(45) Date of Patent: Aug. 14, 2001

(54) AGGREGATES OF SPHERICAL MULTIVALENT METAL ALGINATE MICROPARTICLES AND METHODS OF MAKING THEM

(75) Inventors: Takeshi Hom-ma; Nagayoshi Myo; Takaya Sato, all of Tokyo; Hironobu Nanbu, Mie, all of (JP)

(73) Assignees: Nisshinbo Industries, Inc.; Freund Industrial Co., Ltd., both of (JP)

( * ) Notice: Subject to any disclaimer, the term of this patent is extended or adjusted under 35 U.S.C. 154(b) by 0 days.

(21) Appl. No.: 09/341,052

(22) PCT Filed: Oct. 29, 1998

(86) PCT No.: PCT/JP98/04910

§ 371 Date: Jun. 30, 1999

§ 102(e) Date: Jun. 30, 1999

(87) PCT Pub. No.: WO99/22767

PCT Pub. Date: May 14, 1999

(30) Foreign Application Priority Data

Oct. 31, 1997 (JP) .................................................. 9-314591

(51) Int. Cl.[7] ............................... A61K 9/26; A61K 9/14; A61K 9/16; A61K 9/50
(52) U.S. Cl. .......................... 424/489; 424/469; 424/486; 424/497; 424/498; 424/502
(58) Field of Search .................................... 424/469, 486, 424/489, 497, 498, 502

(56) References Cited

FOREIGN PATENT DOCUMENTS

| 555980 | * 8/1993 | (EP) . |
| 02167220 | 6/1990 | (JP) . |
| 02180709 | * 7/1990 | (JP) . |
| 05039228 | 2/1993 | (JP) . |
| 05222208 | * 8/1993 | (JP) . |

OTHER PUBLICATIONS

Bodmeier, Roland; Spherical agglomerates of water–insoluble drugs; J. Pharm. Sci. 1989, vol. 78 (11), pp. 964–7.*

* cited by examiner

Primary Examiner—Thurman K. Page
Assistant Examiner—S. Tran
(74) Attorney, Agent, or Firm—Fish & Richardson P.C.

(57) ABSTRACT

The present inventors have made studies for the purpose of establishing a process for preparing controlled-release preparations which can rapidly release 99% or more of a slightly soluble medicament (which has by itself shows a slow dissolution rate) in the upper part of the small intestine. As a result, the inventors have succeeded in establishing a process comprising carrying a slightly soluble medicament which has a slow intestinal dissolution rate on aggregates of the spherical microparticles of a multivalent metal alginate, in which each of the secondary particles (i.e., the aggregates) has a specific surface area ranging from 1 to 280 $m^2/g$. This success leads to the accomplishment of the present invention.

14 Claims, 2 Drawing Sheets

AGGREGATES OF SPHERICAL MULTIVALENT METAL ALGINATE MICROPARTICLES AND METHODS OF MAKING THEM

RELATED APPLICATIONS

This application claims the benefit of priority under 35 U.S.C. §371 to Patent Convention Treaty (PCT) International Application Ser. No: PCT/JP98/04910, filed on Oct. 29, 1998, which claims benefit of priority to JP 314591/1997, filed Oct. 31, 1997. The aforementioned applications are explicitly incorporated herein by reference in their entirety and for all purposes.

TECHNICAL FIELD

The present invention relates to a process for processing alginic acid, which has conventionally been used as a thickening agent, a gelatinizing agent and a stabilizing agent in the fields of foods, pharmaceuticals and cosmetics, into a water-insoluble spherical microparticle aggregate applicable to other new fields including chemical industries and agriculture as well as the above-mentioned conventional fields; and an aggregate of multivalent metal alginate microparticles produced by the process. In particular, the present invention relates to an aggregate of multivalent metal alginate microparticles which is suitable as a carrier of a controlled-release preparation and a process for producing the aggregate. More specifically, the present invention relates to a controlled-release preparation which comprises aggregates of multivalent metal alginate microparticles as a carrier and a slightly soluble medicament having a slow dissolution rate carried on the aggregates and which can release the medicament rapidly in the upper part of the small intestine, and a process for producing the controlled-release preparation.

BACKGROUND ART

In the conventional pharmaceutical preparations for oral administration which contains a slightly soluble medicament, the medicament shows a small dissolution rate in the digestive tract. Therefore, the amount of the dissolved medicament per a certain time of period is small, the absorption of the medicament through the digestive tract is delayed, and the amount of the medicament absorbed through the digestive tract per hour becomes small, resulting in slow absorption in a living body and a low bioavailability. In these situations, improvement in solubility of the slightly soluble medicament has been desired for effective manifestation of the efficacy and the quick-acting nature of the medicament.

As examples of the methods previously proposed for improving the solubility of a slightly soluble medicament, Japanese Patent No. 2516524 discloses a method for reducing the particle size of and amorphizing a slightly soluble, crystalline medicament (e.g., nifedipine, indomethacin); and Japanese Patent Application Laid-open Publication No. 54-2316 discloses a method for preparing powders or granules from solid dispersions comprising nifedipine and polyvinylpyrrolidone, which comprises dissolving nifedipine and polyvinylpyrrolidone in an organic solvent (e.g., methanol) to give a solution and then removing the organic solvent therefrom.

Among the commercially available nifedipine preparations, a preparation in which poly(ethylene glycol) is used to form a solid dispersion of nifedipine is "Adalat" (Bayer); and a preparation in which nifedipine is dissolved in an organic solvent and coated on lactose is "Sepamit" (Kanebo, Ltd.).

As a example of amorphization, Japanese Patent Publication No. 54-29565 discloses a method comprising adding a plurality of medicaments including a slightly soluble base medicament into a $\beta$-1,4-glucane and co-ground the medicaments. In this method, the $\beta$-1,4-glucane used is a microcrystalline cellulose "Avicel" (a trade name, Asahi Chemical Industry Co., Ltd.); examples of the slightly soluble base medicament are phenacetin, phenoxymethyl penicillin and phenobarbital; examples of the other medicaments simultaneously used with the base medicament are slightly soluble cortisone acetate, soluble tetracycline hydrochloride and water-soluble pyridoxine hydrochloride; the grinding apparatus for co-grinding of the medicaments is one having mechanisms for mechanically crushing and grinding the medicaments into a microcrystalline form, such as a ball mill; and the co-grinding is continued until the crystalline substances cause no diffraction peak specific to the crystalline substances, that is, from several hours to 10-odd hours which is required for complete amorphization.

Methods for preparing a solid dispersion of nifedipine with an organic solvent are disclosed in Japanese Patent Application Laid-open No. 54-2316 (supra) and Japanese Patent Publication No. 3-7645.

A method for improving the dissolution rate of a slightly soluble medicament is disclosed in Japanese Patent Publication No. 5-66364 in which a slightly soluble medicament and a water-soluble polymer are fed to a twin-roll mill (which is equipped with horizontal two rolls which rotate in opposing directions to each other) through a gap between the rolls while rotating the rolls, and kneaded by the rotation of the rolls.

A method for preparing an easy-absorbable nifedipine preparation which is stable to moisture is disclosed in Japanese Patent Publication No. 3-28404, by which it becomes possible to improve the dissolution properties, particular dissolution rate, of nifedipine in water and, thereby, to produce a preparation stable to moisture compared to the conventional solid solution powdery preparations containing polyvinylpyrrolidone.

This method comprises the steps of granulating a pharmaceutical additive (e.g., lactose) and a water-soluble binder (e.g., polyvinylpyrrolidone) to give a water-soluble fine particulate carrier, spraying a solution of nifedipine and either hydroxypropylmethylcellulose or methylcellulose in a solvent (e.g., ethanol) on the carrier, and then drying the sprayed carrier. The nifedipine preparation provided by this method is one in which nifedipine is coated in the form of a solid dispersion. The preparation thus produced is easy-to-dissolve or easy-to-absorb and is stable to moisture.

A medicament complex comprising a base medicament hardly soluble to water (e.g., phenacetin) which is carried on the surface of a modified starch (e.g., pregelatinized starch), is disclosed in Japanese Patent Publication No. 7-47548. In this patent publication, it is described that the dissolution rate of the base medicament of the medicinal complex is increased as determined by the dissolution test (the second solution, pH 6.8) of the base medicament performed in accordance with the paddle method described in the Japanese Pharmacopoeia Tenth Edition, and thereby the solubility of the base medicament is improved.

A method for improving the dissolution properties of a crystalline medicament that is intestinally slightly soluble to the intestinal juice is disclosed in Japanese Patent Application Laid-open No. 6-227969. This method comprises the steps of dissolving an enteric polymer (e.g., calboxymethylethylcellulose; a product of FREUND INDUSTRIAL CO., LTD.) with a mixed solvent of methylene chloride and ethanol to give a solution, dispersing indomethacin particles (mean particle diameter: 10 μm) or mefenamic acid particles (mean particle diameter: 27 μm) in air as the crystalline medicament particles slightly soluble to the intestinal juice, spraying the above-prepared solution to the particles to adhere the enteric polymer on the particles, and drying the particles.

A method for improving the dissolution properties of a crystalline medicament slightly soluble to water is disclosed in Japanese Patent Application Laid-open No. 7-112928. This method comprises the steps of dissolving nifedipine (mean particle diameter: 20 μm) into ethanol to give a solution, spraying the solution to a hydrophilic substance (e.g., lactose; mean particle diameter: 5–10 μm) to make carry the medicament (i.e., nifedipine) on the hydrophilic substance, granulating the medicament-carried hydrophilic substance together with a water-soluble polymer (e.g., hydroxypropyl cellulose) as a binder.

Alginate gel beads are disclosed in Japanese Patent Application Laid-open No. 2-167220, where a sustained-release preparation is described in which a basic medicament (e.g., nifedipine) is included in the alginate gel beads. In this patent application, the sustained-release preparation is produced by adding a suspension of the basic medicament in a sodium alginate solution to a calcium chloride solution dropwise through a nozzle, keeping the solution to stand, thereby forming alginate gel beads as the sustained-release preparation. In this case, the obtained alginate gel beads are assumed to be converted to calcium alginate gel beads.

Japanese Patent Application Laid-open No. 5-39228 discloses calcium alginate beads containing nifedipine, which is prepared by adding an alginic acid propylene glycol ester and/or sodium alginate to water to give a solution, adding the solution to a calcium chloride solution dropwise through a nozzle, stirring the solution, keeping the resultant solution to stand for 72 hours, washing the solution with water, drying the solution in air, and then further drying the resultant in vacuo at room temperature. The beads thus prepared act as a sustained-release preparation, and is assumed to take a gel form.

Japanese Patent Application Laid-open No. 5-222208 discloses perfectly spherical calcium alginate beads in which alginic acid is ion-crosslinked via bivalent metal ions such as calcium ions and which have a particle size ranging from 0.1 to 30 μm.

Japanese Patent Application Laid-open No. 6-100468 discloses a sustained-release composition comprising a content to be released (e.g., phenytoin, diclofenac sodium, brilliant blue), alginic acid and hyaluronic acid. In this patent application, a typical sustained-release preparation is prepared by adding an aqueous solution containing diclofenac sodium, sodium alginate and hyaluronic acid to a calcium chloride solution dropwise through a nozzle, keeping the solution to stand at room temperature for 24 hours, and washing the solution with distilled water. In this method, it is thought that the sodium alginate used is converted into gelatinous calcium alginate.

Japanese Patent No. 2516524 discloses a method in which nifedipine or indomethacin and crosslinked polyvinylpyrrolidone are ground while mixing continuously for 48 hours with a ball mill to amorphize the nifedipine or indomethacin. This method has such a disadvantage that it requires too much time to grind. Japanese Patent Publication No. 54-29565 discloses a method in which microcrystalline cellulose and a medicament are co-ground until any diffraction peak caused by the crystal structure disappear. This method also has a disadvantage that it requires too much time to co-grind. Therefore, both the methods have a problem in production efficiency.

The method disclosed in Japanese Patent Application Laid-open No. 54-2316 is a wet system with an organic solvent. In the composition produced by this process, nifedipine is present in the state where nifedipine is dissolved in a matrix (e.g., polyvinylpyrrolidone) to form a glassy or solid solution-like structure. Accordingly, the composition is not well satisfactory from the veiwpoint of rapid dissolution of nifedipine in the intestine.

The method disclosed in Japanese Patent Publication No. 5-66364 has a shorter manufacturing period. However, this method requires a heating process. In the method disclosed in Japanese Patent Publication No. 3-28404, the production process is complicated. Accordingly, both of these methods have a problem of increased production cost. In Japanese Patent Publication No. 7-47548, partially pregelatinized starch is exemplified as a preferable carrier. However, the preparation of this patent publication is not also satisfactory as a controlled-release preparation for releasing the medicament in the intestine, because it carries the medicament only on the surface of the starch.

Each of Japanese Patent Application Laid-open Nos. 2-167220, 5-39228, 6-100468 and 6-25013 discloses a controlled-release preparation in which a medicament is included in calcium alginate gel beads.

Japanese Patent Application Laid-open Nos. 6-227969 and 7-112928 disclose processes performed in air. The processes are not suitable for mass production.

Accordingly, the object of the present invention is to provide a controlled-release preparation capable of rapidly releasing a slightly soluble medicament that has a slow intestinal dissolution rate in the intestine and a process for preparing the controlled-release preparation. Another object of the present invention is to provide a controlled-release preparation capable of releasing in the intestine 99% or more of the slightly soluble medicament from the carrier and a process for preparing the controlled-release preparation.

DISCLOSURE OF THE INVENTION

The present inventors have studies for the purpose of establishing a process for preparing a controlled-release preparation capable of releasing in the upper part of the small intestine 99% or more of a slightly soluble medicament that has a slow intestinal dissolution rate by itself. As a result, the inventors have succeeded in establishing a process for making carry a slightly soluble medicament that has a slow intestinal dissolution rate by itself on aggregates of spherical microparticles of multivalent metal alginate in which each of the secondary particles has a specific surface area ranging from 1 to 280 $m^2/g$. This success leads to the accomplishment of the present invention.

That is, the present invention encompasses the invention comprised of the following technical subjects.

(1) An aggregate of spherical microparticles of a multivalent metal alginate, comprising a secondary particle which is an aggregate of primary particles of the multivalent metal alginate, wherein the mean particle diameter of the primary particles is within the range from 0.01 to 5 μm inclusive, and the specific surface area of the secondary particle is within the range from 1 to 280 $m^2/g$ inclusive.

(2) The aggregate of item (1), wherein the multivalent metal alginate is calcium alginate.

(3) The aggregate of item (1) or (2), wherein the primary particles have a mean particle diameter ranging from 0.01 to 5 μm inclusive, preferably from 0.05 to 1 μm inclusive, and each of the secondary particle has a specific surface area ranging from 1 to 5 $m^2/g$ inclusive.

(4) A process for preparing aggregates of spherical microparticles of a multivalent metal alginate, which comprises the steps of:

adding an aqueous sodium alginate solution and/or an aqueous alginic acid solution to a non-aqueous solvent mainly comprising a polyhydric alcohol fatty acid ester, and then adding an emulsifying agent to the formed mixture so as to cause emulsion-dispersion, thereby forming a water-in-oil (W/O) type emulsion;

adding an aqueous solution of a multivalent metal salt to the emulsion to form spherical microparticles of the multivalent metal alginate; and spray-drying a suspension of the spherical microparticles in water, thereby forming aggregates of the spherical microparticles.

(5) The process of item (4), wherein the aggregate is a secondary particle which is an aggregate of the primary particles of the spherical microparticles having a mean particle diameter ranging from 0.01 to 5 μm inclusive, and wherein the aggregate has a specific surface area ranging from 1 to 280 $m^2/g$ inclusive.

(6) The process of item (4) or (5), wherein the polyhydric alcohol fatty acid ester is at least one compound selected from the group consisting of glycerol fatty acid esters and propylene glycol fatty acid esters, the constituent fatty acid of the ester having 18 or less carbon atoms and a melting temperature of 50° C. or less.

(7) The process of any one of items (4) to (6), wherein the emulsifying agent is at least one compound selected from the group consisting of sorbitan fatty acid esters, polyglycerol fatty acid esters and polylycinoleic acid polyglycerol esters.

(8) The process of any one of claims (4) to (7), wherein the multivalent metal is at least one metal having a valency of 2 or more selected from the group consisting of calcium, zinc, beryllium, copper, barium, cadmium, strontium, radium, iron, aluminum, cobalt, nickel, chromium and manganese.

(9) The process of any one of claims (4) to (8), wherein the multivalent metal is calcium.

(10) A controlled-release preparation comprising aggregates of spherical microparticles of a multivalent metal alginate, together with a slightly soluble medicament carried on the aggregates, wherein the aggregate is a secondary particle which is an aggregate of the primary particles of the multivalent metal alginate, the mean particle diameter of the primary particles is within the range from 0.01 to 5 μm inclusive, and the specific surface area of the secondary particle is within the range from 1 to 280 $m^2/g$ inclusive.

(11) The controlled-release preparation of item (10), wherein the slightly soluble medicament is at least one compound selected from the group consisting of acetaminophen, aspirin, indomethacin, ethenzamide, ibuprofen and diclofenac sodium.

(12) The controlled-release preparation of item (10) or (11), wherein the multivalent metal alginate is calcium alginate, and the slightly soluble medicament is carried on the aggregates of the spherical microparticles of calcium alginate.

(13) The controlled-release preparation of any one of items (10) to (12), which comprises 1 part by weight of the aggregates of the spherical microparticles of the calcium alginate and 0.01 to 10 parts by weight of the slightly soluble medicament.

(14) The controlled-release preparation of any one of items (10) to (13), wherein the dissolution rate of the slightly soluble medicament in the artificial intestinal juice (the second solution, pH 6.8) is 99% or more within 30 minutes.

(15) The controlled-release preparation of any one of items (10) to (14), wherein the dissolution rate of the slightly soluble medicament in the artificial intestinal juice (the second solution, pH 6.8) is 95% or more within 15 minutes.

(16) A process for preparing a controlled-release preparation of any one of items (10) to (15), which comprises mixing the aggregates of the spherical microparticles of the multivalent metal alginate with the slightly soluble medicament in a dry system.

(17) A process for preparing a controlled-release preparation of any one of items (10) to (16), which comprises mixing the aggregates of the spherical microparticles of the multivalent metal alginate with the slightly soluble medicament in a wet system.

(18) The process of item (16) or (17), wherein the aggregate of the spherical microparticles of the multivalent metal alginate is of calcium alginate.

BEST MODE FOR CARRYING OUT THE INVENTION

Figure 1:
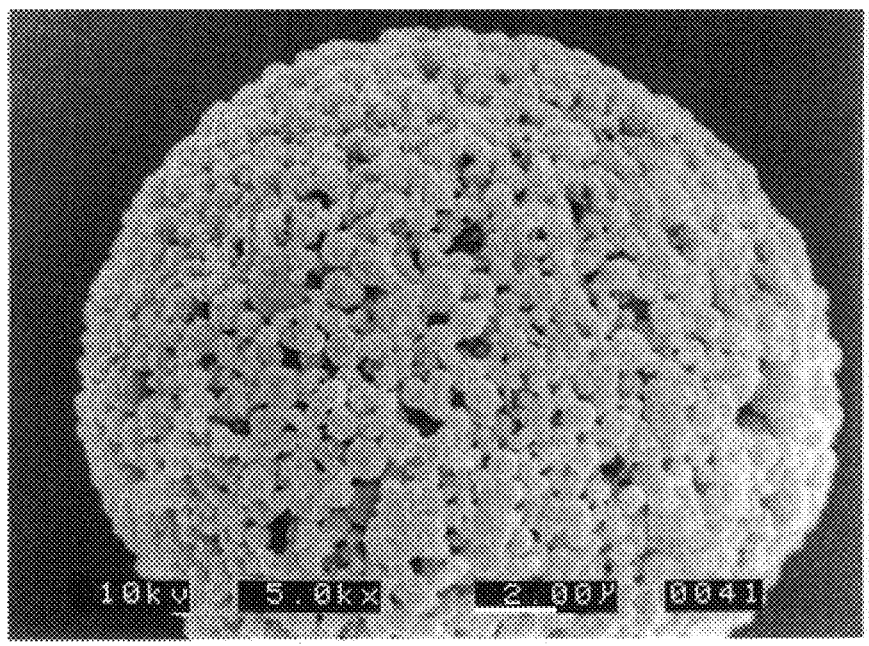
FIG. 1 is a photograph showing the surface of CAB observed under a scanning electron microscope (magnification: 5000 times)

The microparticles of the multivalent metal alginate used as the primary particles in the aggregates of the present invention are microparticles of an alginate of a metal having a valency of two or more selected from the group consisting of calcium, zinc, beryllium, copper, barium, cadmium, strontium, radium, iron, aluminum, cobalt, nickel, chromium and manganese, which have a mean particle diameter ranging from 0.01 to 5 μm, preferably ranging from 0.05 to 1.0 μm.

The primary particles comprising the multivalent metal alginate microparticles can be prepared by the steps of mixing an aqueous solution of a seaweed-derived alginic acid with a polyhydric alcohol fatty acid ester selected from the group consisting of a glycerol fatty acid ester and a propylene glycol fatty acid ester to form a water-in-oil (W/O) type emulsion; mechanically dispersing the W/O type emulsion into a non-aqueous solvent containing at least one emulsifying agent selected from the group consisting of a sorbitan fatty acid ester, a polyglycerol fatty acid ester and a poly(lecinoleic acid) polyglycerol ester to make the W/O type emulsion stable, thereby forming a stable W/O type emulsion; and emulsion-mixing the stable W/O type emulsion with an aqueous solution of at least one metal salt which is capable of forming a water-insoluble product when reacted with an alginic acid, where the metal is a bivalent metal selected from the group consisting of calcium, zinc, beryllium, copper, barium, cadmium, strontium and radium or a metal having a valency of three or more selected from the group consisting of iron, aluminum, cobalt, nickel, chromium and manganese.

The seaweed-derived alginic acid used for preparation of the primary particles is a long-chain copolymer (molecular weight: 4,000–180,000) of D-mannuronic acid and L-glucuronic acid, and is used in the form of 0.1–5 wt %, preferably 0.5–2 wt % of an aqueous solution. The alginic acid may also be used in the form of an alkali metal salt which exhibits a good solubility, such as sodium alginate.

The polyhydric alcohol fatty acid ester, which constitutes an oil-based continuous layer of the emulsion, is preferably those having a dynamic interfacial tension against water as low as possible, so that the particle diameters of the W/o emulsion particles can be adjusted to those of sub-micron orders. Preferably, in the polyhydric alcohol fatty acid ester, the constituent fatty acid has 18 or less of carbon atoms and a melting temperature of 50° C. or less. Preferable example of the polyhydric alcohol fatty acid ester include fatty acid glycerides such as oleic acid mono- or di-glycerides and linoleic acid mono- or di-glycerides; organic acid monoglycerides each comprising any of these mono-glycerides into which an organic acid (e.g., citric acid, succinic acid, malic acid, diacetyltartaric acid) is introduced; and triglycerides of middle-chain (C6–C12) fatty acids. Besides, propylene glycol fatty acid esters are also preferable, including caprylic acid mono- or di-esters, capronic acid mono- or di-esters, and organic esters each comprising any of these esters into which an organic acid (e.g., citric acid, succinic acid, malic acid, diacetyltartaric acid) is introduced.

These polyhydric alcohol fatty acid esters are safe and have superior in processability because they show no volatility or inflammability at ordinary temperatures.

The sorbitan fatty acid ester used as an emulsifying agent preferably has an esterification degree ranging from about 20% to about 75%. The constituent fatty acid of the sorbitan fatty acid ester is preferably an unsaturated fatty acid, such as oleic acid, linolic acid, linolenic acid, or a mixture thereof.

The polyglycerol fatty acid ester preferably has an esterification degree ranging from about 20% to about 75% and a condensation degree of the polyglycerol ranging from 2 to 10. Especially preferable example of the polyglycerol fatty acid ester include diglycerol monooleate, triglucerol dioleate, tetraglycerol trioleate, pentaglycerol tetraoleate, hexaglycerol tetraoleate, hexaglycerol pentaoleate, decaglycerol pentaoleate and decaglycerol heptaoleate.

The poly(ricinoleic acid) polyglycerol fatty acid ester preferably has a condensation degree of the ricinoleic acid ranging from 2 to 6 and a condensation degree of the polyglycerol ranging from 4 to 10.

The multivalent metal salt which is cable of forming a water-insoluble product when reacted with the alginic acid can be prepared as a 1–20 wt % aqueous solution or a 1–20 wt % water-containing alcohol solution. The multivalent metal salt may be any one selected from the salts of the metals each having a valency of 2 or more, such as calcium, zinc, beryllium, copper, barium, cadmium, strontium, radium, iron, aluminum, cobalt, nickel, chromium and manganese, or may be used as a mixture of two or more of these metals. The multivalent metal salt is contacted with the W/O micelle of the alginic acid in the form of a W/O micelle to cause cross-bonding between the two carboxyl groups in the alginic acid, thereby forming water-insoluble spherical microparticles of the metal alginate.

After the formed spherical microparticles of the metal alginate are treated to make them insoluble, the spherical microparticles are excluded out of the W/O emulsion system by further adding the same aqueous multivalent metal salt solution as used just before this procedure to the emulsion system in an amount three times or larger. Thus the spherical microparticles can be collected from the oil-based continuous layer easily with a centrifuge capable of providing an acceleration of gravity of 1500×g or more. The collected spherical alginate microparticles are washed with hot water to remove the undesired substances remaining on the surfaces and the insides of the microparticles, such as the emulsifying agent, the multivalent metal salts and the low molecular alginic acid components which are not used for the cross-linkage.

The primary particle, which is the spherical microparticle of a multivalent metal alginate of the present invention, is characterized by having mean particle diameter ranging from 0.01 to 5 $\mu$m. The above-mentioned secondary particle, which is an aggregate of the primary particle, may be suitable as carriers for a controlled-release preparation. The primary particles may also be used as an additive for a coating film having a thickness of sub-micron order or for a synthetic fiber. Therefore, the primary particles may also be applicable as useful spherical microparticles in the fields that attach importance to feelings, such as the filed of skin cosmetics where it is required for the diameters of the particles to be 10 $\mu$m or smaller which are perceptible by a human.

The primary particles of the present invention, which comprise the spherical multivalent metal alginate microparticles, are suspended into water and then spray-dried to cause aggregation of the particles and to thereby form larger secondary particles. Thus, aggregates of the spherical metal alginate microparticles each having a specific surface area ranging from 1 to 280 $m^2/g$ can be produced.

The aggregate of the spherical multivalent metal alginate microparticles preferably used in the present invention is an aggregate of spherical calcium alginate microparticles [hereinafter, simply referred to as "calcium alginate bead" or "CAB"]. CAB can be produced by granulating sodium alginate extracted from a brown seaweed, such as sea tangle (the genus Laminaria) and edible seaweed (the genus Eisenia), into nearly perfectly spherical forms and then making the granule insoluble with calcium ions, of which the primary particles have a mean particle diameter ranging from 0.01 to 5 $\mu$m, preferably ranging from 0.05 to 1 $\mu$m, and the secondary particle has a specific surface area ranging from 1 to 280 $m^2/g$, preferably ranging from 1 to 50 $m^2/g$, more preferably ranging from 1 to 5 $m^2/g$, as measured by the BET method. As commercially available CAB, "Flavikafine" (a trade name; Nisshinbo Industries, Inc.) is preferably used.

In the aggregates of the spherical multivalent metal alginate microparticles of the present invention, if the mean particle diameter of the primary particles is smaller than 0.01 $\mu$m, the adsorbing properties of a slightly soluble medicament to the aggregates becomes poor; whereas if the mean particle diameter of the primary particles is larger than 5am, the physical strength of the aggregates becomes weak, resulting in breakage of the aggregates during mixing with a medicament. In addition, if the specific surface area of the secondary particle is less than 1 m²/g, the physical strength of the aggregates becomes weak, resulting in breakage of the aggregates during mixing with a medicament; whereas if the specific surface area is larger than 280 m²/g, the adsorbing properties of the medicament to the aggregates becomes poor. Therefore, the mean particle diameter of the primary particles and the specific surface area of the secondary particle not falling within the above-mentioned ranges are not preferable.

When CAB, which is an aggregate of the spherical multivalent metal alginate microparticles preferably used in the present invention, were determined on the mean particle diameter distribution with a laser diffraction/scattering-type mean particle diameter analyzer ("HEROS"; Sysmpatec) on a volume base, it was found that CAB has a mean particle diameter ranging from 5 to 50 μm when dispersed in a dry system (without a solvent) and from 0.5 to 5 μm when dispersed in water.

When the particle diameter of CAB was determined by observation under a scanning electron microscope, it was found that the CAB was dispersed in water almost in the form of primary particles, whereas the primary particles of the CAB were aggregated to form porous secondary particles in the dry state or when dispersed in ethanol.

Figure 2:
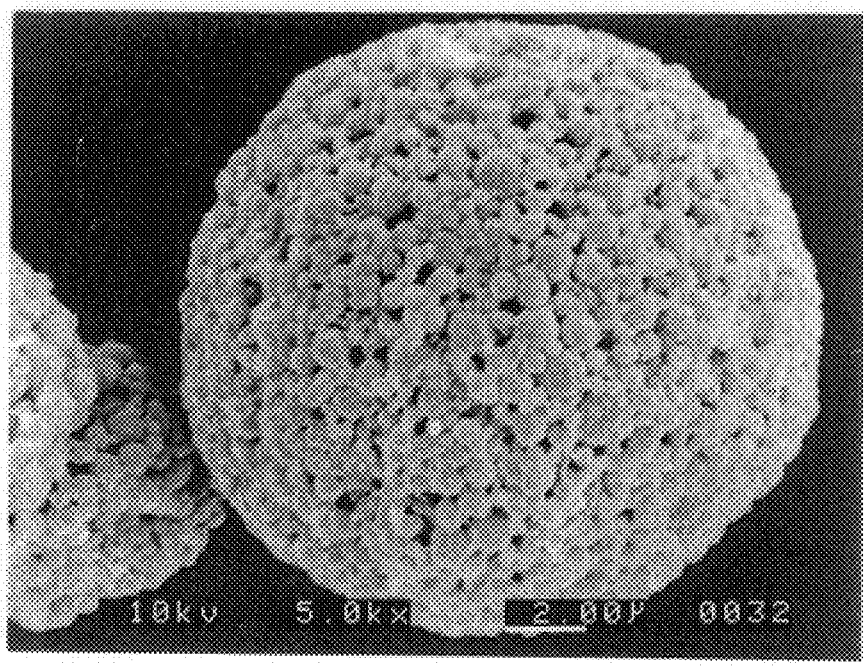
FIG. 2 is a photograph showing the surface of AAP-carried CAB observed under a scanning electron microscope (magnification: 5000 times).

Furthermore, as shown in FIGS. 1 and 2, the CAB of the present invention takes the form of not a gel but secondary particles. Therefore, the mechanism for releasing a medicament of the CAB is different from gel-type carriers. As shown in FIG. 2, the medicament-carried CAB also form secondary particles, where the medicament is carried in a quite different way than the glassy carriers or the solid solution-type carriers. Moreover, the controlled-release preparation comprising the CAB and a slightly soluble medicament carried thereon of the present invention is also different from a preparation in which a medicament is carried on the surface of a single-particle carrier (e.g., starch), and has a novel structure that has not been found previously.

As shown in the scanning electron microscopic photographs given in the examples below, the CAB takes a nearly perfectly spherical form. In general, it is preferable that powders used as a raw material of a pharmaceutical preparation take the nearly perfectly spherical form (in other words, have an aspect ratio of nearly 1) so that the powders exhibit good flowability and quantitative property. This is because it is necessary for the powders to reduce the weight variation during transportation or supply of the powders to a hybridizing apparatus. As used herein, the aspect ratio refers to the ratio between the lengths of the long axis and the short axis of a particle, which is a measure of sphericity degree. The long axis/short axis ratio is obtained by placing particles randomly on a slide grass, taking a picture of the particles to measure the length of the long axis (the longer diameter) and the length of the short axis (the shorter diameter; determined by drawing a line perpendicular to the long axis at its midpoint) for each of 50 particles, calculating the ratio of the length of the long axis to the length of the short axis for each particle, and then averaging the calculated values of the 50 particles. The secondary particle of the CAB preferably used in the present invention characteristically also has an aspect ratio of nearly 1, which is 1.2 or less and preferably 1.1 or less.

The controlled-release preparation according to the present invention can be prepared by making carry a slightly soluble medicament on the aggregates of the spherical multivalent metal alginate microparticles produced by the process mentioned above.

The slightly soluble medicament used in the present invention may be any substance that exhibits a medicinal efficacy, is pharmaceutically acceptable, is confirmed to the Japanese Pharmacopoeia (the 13th Amendment) and requires 30 ml or more of water to dissolve 1 g of the substance.

Examples of the slightly soluble medicament include acetaminophen, aspirin, indomethacin, ethenzamide and nifedipine. The solubilities of these substances in water are shown in Table 1, respectively. The unit of each numerical value shown in Table 1 is the weight (mg) of each of the slightly soluble medicaments capable of dissolving in 1 m of the solvent (water).

As used herein, the term "solubility" in accordance with the Japanese Pharmacopoeia (the 13th Amendment) refers to the degree of dissolution of a medicament in a solvent within 30 minutes when 1 g of the medicament is added to the solvent and mixing them with vigorous shaking at intervals of 5 minutes at 20° C.±5° C. In the present specification, the solubility is evaluated in accordance with this method. When the amount (ml) of water required to dissolve 1 g of a medicament is 30 ml or more, the solubility of the medicament represents the grades of "slightly soluble" or "hardly soluble". In accordance with the standard of the U.S. Pharmacopoeia 21 (1985), the term "slightly soluble" is defined as "sparingly soluble".

TABLE 1

| Slightly soluble medicament | (unit: mg/ml) Water |
|---|---|
| Acetaminophen | 13.1 |
| Aspirin | 3.63 |
| Indomethacin | less than 0.1 |
| Ethenzamide | less than 0.1 |

In the controlled-release preparation of the present invention, a medicament selected from the group consisting of acetaminophen, aspirin, indomethacin, ethenzamide, ibuprofen and diclofenac sodium or a combination of two or more of them is carried as a slightly soluble medicament on the aggregates of spherical calcium alginate microparticles such as the CAB mentioned above. The controlled-release preparation carries 0.01 to 10 parts by weight of the slightly soluble medicament per 1 part by weight of the CAB.

The controlled-release preparation of the present invention is also characterized in that a dissolution rate of the slightly soluble medicament in the artificial intestinal juice (the second solution, pH 6.8) is 99% or more within 30 minutes.

The controlled-release preparation of the present invention is also characterized in that a dissolution rate of the slightly soluble medicament in the artificial intestinal juice (the second solution, pH 6.8) is 95% or more within 15 minutes.

The controlled-release preparation of the present invention may be formulated into tablets with an excipient, or powders or granules by granulating the medicament-carried CAB. The tables, powders or granules may be coated with an enteric coating film material to provide an enteric preparation. The granules may also be encapsulated into capsules.

The controlled-release preparation of the present invention can be prepared by hybridizing the slightly soluble medicament with the aggregates of spherical multivalent metal alginate microparticles in a dry system or a wet system.

In the preparation of the controlled-release preparation of the present invention, the term "dry system" means a system without any solvent (e.g., water, an organic solvent), and the term "wet system" means a system with a solvent (e.g., water, an organic solvent).

The organic solvent used in the present invention is ethanol alone or a mixed solvent of, for example, water-containing ethanol or a mixed solvent such as that of ethanol and methylene chloride. However, in general, ethanol alone is preferably used.

By employing a wet system, it become possible to include the medicament within the secondary particles of the aggregates of the spherical multivalent metal alginate microparticles. In other words, the secondary particles of the CAB can carry the medicament in the spaces between the primary particles constituting the secondary particles and, thereby, act as a microsponge and exhibit porous substance-like functions.

As used herein, the term "hybridizing" or "to hybridize" means a procedure to contact a medicament with the aggregates of the spherical multivalent metal alginate microparticles in order to make carry the medicament on the aggregates. In the present invention, this term means a processing for making carry a slightly soluble medicament on the aggregates by a simple mixing, a mixing optionally accompanied by grinding of the medicament, an emulsion dispersion, a spray drying and other processing techniques such as an air suspension coating (a process for preparing microcapsules).

In the present invention, the mixing accompanied by grinding of the medicament can be performed with a conventional mixer or a mixing-grinder. Examples of the grinder include, not limited to, a ball mill (such as a product of Kurimoto, Ltd.), a vertical jet mill (e.g., a product of Seishin Enterprise Co., LTD.), a planetary ball mill (e.g., a product of Seishin Enterprise CO., LTD.), a vibrating mill (e.g., a product of Chuo Kakohki CO., LTD.). As a matter of course, in the hybridizing process accompanied by grinding of the medicament, such processing conditions are selected that cause no or, if any, less disintegration of the spherical aggregates (the secondary particles) of the multivalent metal alginate microparticles of the present invention.

By the hybridizing process of the present invention, the medicament can be carried on the surfaces of the aggregates of the spherical multivalent metal alginate microparticles and in the spaces between the microparticles. When put into water, the medicament-carried aggregates thus prepared are disintegrated into the primary particles and dispersed in water.

The "drying" performed in the hybridizing process in the preparation of the controlled-release preparation of the present invention means to distill off the solvent (e.g., water, an organic solvent), and generally a drying procedure performed in a spray-drying apparatus is applicable. Any type of the spray-drying apparatus may be used as long as the solvent can be distilled off by spraying a solution containing the solvent and the aggregates of the spherical multivalent metal alginate microparticles in hot air, such as spray dryers produced by Ohkawara Kakohki Co., Ltd. and ASHIZAWA-NIRO ATOMIZER LTD.

The temperature of the dry air in the spray-drying apparatus is preferably not higher than 250° C. from the viewpoint of providing appropriate stability of the slightly soluble medicament and not lower than 100° C. from the viewpoint of drying efficacy. The spraying is performed with an atomizer equipped with, for example, a rotary disk, a twin-flow nozzle, a nozzle or an airless nozzle.

When an atomizer equipped with a nozzle is used, the mean particle diameter distribution of the aggregates of the spherical multivalent metal alginate microparticles with a slightly soluble medicament carried thereon becomes sharper compared to the case where an atomizer equipped with a rotary disk is used. Therefore, an atomizer equipped with a nozzle is preferable.

Besides the above-mentioned spray-drying apparatus, any other type of apparatus may be used as long as the destruction of the secondary particle structure of the aggregates of the spherical multivalent metal alginate microparticles does not occur, and a statistic drying apparatus or a fluid-bed drying apparatus may be employed appropriately.

As used herein, the term "artificial intestinal juice (the second solution, pH 6.8)" refers to a phosphate buffer of pH 6.8 as described in the Japanese Pharmacopoeia (the 13th Amendment), the section of dissolution test, the second method (paddle method). As used herein, the term "dissolution rate" refers to a value given by dividing the actual elution concentration of a slightly soluble medicament by the calculated elution concentration and expressing the resultant value as a percent. Here, the term "calculated elution concentration" refers to the concentration given when hypothesizing that the entire slightly soluble medicament added to the second solution is dissolved. For example, the calculated elution concentration of a slightly soluble medicament given when 5 g of the medicament is added to 500 ml of the second solution is 10 mg/ml. In this case, when the actual elution concentration is 5 mg/ml, the dissolution rate is 50%.

Figure 3:
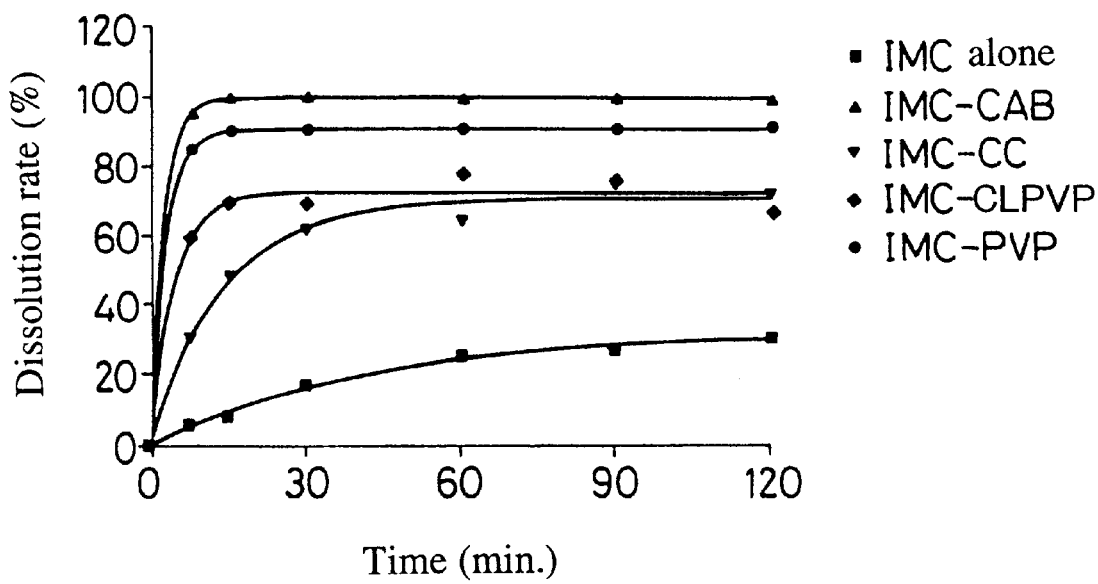
FIG. 3 is a graphical illustration showing the dissolution rates of a slightly soluble medicament carried on various carriers.

In general, the dissolution rate of a slightly soluble medicament by itself is slow in the artificial intestinal juice, and the saturated dissolution amount is small. Therefore, the saturated dissolution concentration tends to be smaller than the calculated concentration. For example, as shown in FIG. 3, indomethacin by itself shows a dissolution rate of less than 40% even within two hours.

The present invention will be described more in detail below by the embodiments where CAB is used as the aggregate of the spherical multivalent metal alginate microparticles. However, the present invention should not be construed to be limited by the following examples.

EXAMPLE 1

There were provided an aqueous sodium alginate solution (the dispersed phase; 1 liter) in which the concentration of sodium alginate was adjusted to 5 wt % and a non-aqueous solvent (the continuous phase; 4 liters) which contained poly(ricinoleic acid) polyglycerol ester in propylene glycol dicapric acid ester in a concentration of 10 wt %.

The dispersed phase and the continuous phase were emulsified with each other with a homomixer (10000 rpm, 10 minutes) while pouring the dispersed phase into the continuous phase to give a W/O-type emulsion.

The W/O-type emulsion was emulsion-mixed with a 20 wt % aqueous solution of calcium chloride (1 liter) with a homomixer (10000 rpm, 10 minutes) while pouring the aqueous calcium chloride solution into the W/O-type emulsion to cause crosslinking.

The emulsion mixture thus obtained was further mixed with a 20 wt % aqueous solution of calcium chloride (10 liters) with a homomixer (10000 rpm, 10 minutes) and then subjected to centrifugation (1500×g, 10 minutes) to collect spherical microparticles of calcium alginate. The spherical microparticles thus collected were washed with hot water and then suspended into water to give a suspension. The suspension was then spray-dried.

It was confirmed that the spherical calcium alginate microparticles dispersed into water had a mean particle diameter of 0.05 µm as determined with a laser diffraction type particle distribution analyzer and took the form of spherical particles as observed under an electron microscope.

EXAMPLE 2

There were provided an aqueous sodium alginate solution (the dispersed phase; 1.5 liters) in which the concentration of sodium alginate was adjusted to 10 wt % and a non-aqueous solvent (the continuous phase; 3.5 liters) which contained poly(ricinoleic acid) polyglycerol ester in a middle-chain fatty acid triglyceride in a concentration of 5 wt %.

The dispersed phase and the continuous phase were emulsified with each other with a homomixer (10000 rpm, 1 minutes) while pouring the dispersed phase into the continuous phase to give a W/O-type emulsion.

The W/O-type emulsion was emulsion-mixed with a 20 wt % aqueous solution of calcium chloride (2 liters) with a homomixer (10000 rpm, 10 minutes) while pouring the aqueous calcium chloride solution into the W/O-type emulsion to cause crosslinking.

The emulsion mixture thus obtained was further mixed with a 20 wt % aqueous solution of calcium chloride (6 liters) with a homomixer (10000 rpm, 10 minutes) and then subjected to centrifugation (1500×g, 10 minutes) to collect spherical microparticles of calcium alginate. The spherical microparticles thus collected were washed with hot water and then suspended into water to give a suspension. The suspension was then spray-dried.

It was confirmed that the spherical calcium alginate microparticles dispersed into water had a mean particle diameter of 1.0 µm as determined with a laser diffraction type particle distribution analyzer and took the form of spherical particles as observed under an electron microscope.

EXAMPLE 3

There were provided an aqueous sodium alginate solution (the dispersed phase; 2.5 liters) in which the concentration of sodium alginate was adjusted to 10 wt % and a non-aqueous solvent (the continuous phase; 2.5 liters) which contained sorbitan monooleic acid ester in a middle-chain fatty acid triglyceride in a concentration of 2 wt %.

The dispersed phase and the continuous phase were emulsified with each other with a homomixer (10000 rpm, 1 minutes) while pouring the dispersed phase into the continuous phase to give a W/O-type emulsion.

The W/O-type emulsion was emulsion-mixed with a 20 wt % aqueous solution of calcium chloride (2 liters) with a homomixer (10000 rpm, 10 minutes) while pouring the aqueous calcium chloride solution into the W/O-type emulsion to cause crosslinking.

The emulsion mixture thus obtained was further mixed with a 20 wt % aqueous solution of calcium chloride (6 liters) with a homomixer (10000 rpm, 10 minutes) and then subjected to centrifugation (1500×g, 10 minutes) to collect spherical alginate microparticles. The spherical alginate microparticles thus collected were washed with hot water and then suspended into water to give a suspension. The suspension was then spray-dried.

It was confirmed that the spherical alginate microparticles dispersed into water had a mean particle diameter of 5.0 µm as determined with a laser diffraction type particle distribution analyzer and took the form of spherical particles as observed under an electron microscope.

EXAMPLE 4

The slightly soluble medicament acetaminophen (KONGO YAKUHIN CO., LTD., hereinafter simply referred to as "AAP"; 6 g) was dissolved in ethanol (JP grade) to give a solution (50 ml). To this solution was gradually added the carrier calcium alginate beads (Nisshinbo Industries Inc.; a trade name "Flavikafine SF-D", hereinafter simply referred to as "CAB"; 1.0 g) and subjected to isotonification for 30 minutes. The solution was centrifuged at 3000 rpm for 20 minutes. Subsequently the sedimented CAB particles were dried at rest at 105° C. for 4 hours to give the CAB with AAP carried thereon (hereinafter, simply referred to as "AAP-carried CAB).

FIG. 1 shows a photograph of the CAB magnified 5000 times by a scanning electron microscope. As is evident from the photograph, the CAB is a spherical microgranule in which the primary particles having particle diameter ranging from 0.2 to 1.0 µm are aggregated to form the secondary particle. The median diameter (D50) of the CAB was 14.2 µm. The secondary particle of the CAB has an aspect ratio of 1.1, which means that the CAB was a nearly true sphere.

FIG. 2 shows a photograph of the AAP-carried CAB magnified 5000 times by a scanning electron microscope. As is evident from the photograph, each of the AAP-carried CAB particles is a spherical microgranule in which the primary particles having particle diameter ranging from 0.2 to 1.0 µm are aggregated to form the secondary particle. The median diameter (D50) of the AAP-carried CAB was 14.3 µm. The secondary particle of the AAP-carried CAB has an aspect ratio of 1.1, which means that the AAP-carried CAB was a nearly true sphere.

The AAP content of the AAP-carried CAB was determined by the following manner.

That is, the AAP-carried CAB (100 mg) is dispersed into ethanol (JP grade) (100 ml) and then subjected to isotonification for 30 minutes. The dispersion is centrifuged (3000 rpm, 20 minutes) to give an extract of AAP. The extract is subjected to determination of absorbance at an absorption wavelength of 244 nm with a spectrophotometer.

As a result, it was found that the AAP content of the AAP-carried CAB was 16.0% (w/w).

EXAMPLE 5

The same procedure as Example 1 was repeated, except that the slightly soluble medicament aspirin (a product of KOZAKAI SEIYAKU CO., LTD.; hereinafter, simply referred to as "AS") was used in place of AAP to give AS-carried CAB. The photograph of the AS-carried CAB magnified 5000 times by a scanning electron microscope was similar to that shown in FIG. 2. The AS content of the AS-carried CAB was 16.1% (w/w) as determined by the same procedure as Example 1 except that an absorption wavelength of 278 nm was employed.

EXAMPLE 6

A slightly soluble medicament indomethacin (a product of DAIWA PHARMACEUTICAL CO., LTD,; hereinafter, simply referred to as "IMC") (500 mg) was added to the CAB and the resultant mixture was ground while mixing with an automatic mortar (a product of Nitto Scientific CO., LTD.) at room temperature for 1 hour.

A portion (100 mg; corresponding to 50 mg in terms of IMC) of the mixing-ground product was sampled and tested in accordance with the Japanese Pharmacopoeia (the 13th Amendment), the second method of the dissolution test (i.e., the paddle method) as follows.

That is, the number of revolution of the paddle was fixed to 100 rpm, and the mixing-ground product (100 mg) was added to the second solution (a phosphate buffer; pH 6.8, 500 ml) to give a solution, and the test was conducted at 37° C.

After addition of the mixing-ground product to the second solution, a portion of the solution was sampled once every a predetermined period of time, and each of the sample solutions was filtered with a membrane filter (pore size: 0.2 μm). A portion (5 ml) of the filtrate was removed, extracted with chloroform (5 ml), and then centrifuged. The chloroform layer given after the centrifugation was used for determination of the absorbance of IMC with a spectrophotometer at a wavelength of 318 nm. The determination procedure was conducted twice and the two results obtained were averaged (the variation of the results was small). The results are shown in FIG. 3.

The dissolution rate of the IMC-carried CAB to the first solution (pH 1.2) was also determined in the same manner as above. As a result, it was found that IMC was less released from the IMC-carried CAB and the dissolution rate within 2 hours was less than 1%.

EXAMPLE 7

Figure 4:
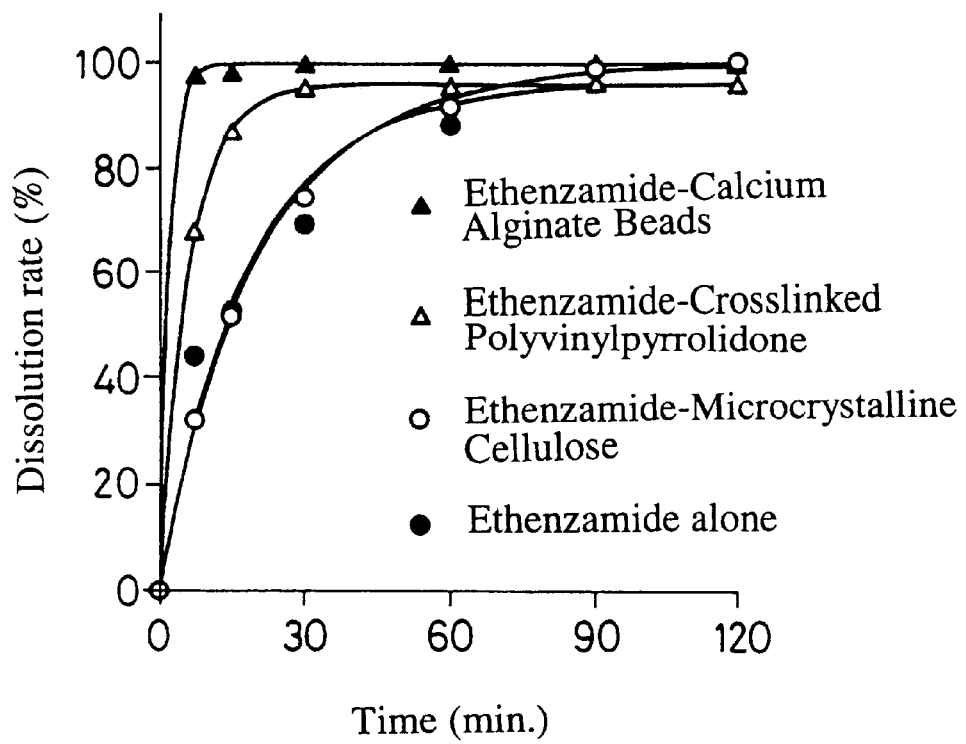
FIG. 4 is a graphical illustration showing the dissolution rates of a slightly soluble medicament carried on various carriers.

Ethenzamide (a product of SHIZUOKA COFFEIN & CO, LTD.; hereinafter, simply referred to as "EZ") was used as the slightly soluble medicament in place of IMC. EZ (500 mg) was added to the CAB (500 mg) and the resultant mixture was ground while mixing with an automatic mortar at room temperature for 1 hour. A portion (50 mg; corresponding to 25 mg in terms of EZ) of the mixing-ground product obtained was subjected to the same procedure as Example 3 to determine the EZ content of the product. The wavelength employed in the determination process was 290 nm. The results are shown in FIG. 4.

COMPARATIVE EXAMPLE 1

Crystalline cellulose ("Avicel PH-M06", a product of Asahi Chemical Industry, Co., Ltd.; hereinafter, simply referred to as "CC") was used as a carrier. The slightly soluble medicament IMC (500 mg) was added to the CC (500 mg) and the resultant mixture was ground while mixing with an automatic mortar at room temperature for 1 hour. A portion (100 mg; corresponding to 50 mg in terms of IMC) of the mixing-ground product obtained was subjected to the same procedure as Example 3 to determine the IMC content of the product. The wavelength employed in the determination process was 318 nm. The results are shown in FIG. 3.

COMPARATIVE EXAMPLE 2

Crosslinked polyvinylpyrrolidone ("Polyplasdone XL", a product of GAF; hereinafter, simply referred to as "CLPVP") and polyvinylpyrrolidone (hereinafter, simply referred to as "PVP") (500 mg each) were separately added to the slightly soluble medicament IMC (500 mg), and each of the resultant mixtures was ground while mixing with an automatic mortar at room temperature for 1 hour. A portion (100 mg; corresponding to 50 mg in terms of IMC) of each of the mixing-ground products obtained was subjected to the same procedure as Example 3 to determine the IMC content of each of the products. The wavelength employed in the determination process was 318 nm. The results are shown in FIG. 3.

COMPARATIVE EXAMPLE 3

The same procedure as Example 6 was repeated, except that IMC alone (50 mg) was used in place of the mixing-ground product (100 mg; corresponding to 50 mg in terms of IMC) to determine the IMC content of the product. The results are shown in Table 3.

COMPARATIVE EXAMPLE 4

Crystalline cellulose ("Avicel PH-M06", a product of Asahi Chemical Industry Co., Ltd.; hereinafter, simply referred to as "CC") (500 mg) was added to the slightly soluble medicament EZ (500 mg) and the resultant mixture was ground while mixing with an automatic mortar at room temperature for 1 hour. A portion (50 mg; corresponding to 25 mg in terms of EZ) of the mixing-ground product obtained was subjected to the same procedure as Example 6 to determine the EZ content of the product. The wavelength employed in the determination process was 290 nm. The results are shown in FIG. 4.

COMPARATIVE EXAMPLE 5

Either of crosslinked polyvinylpyrrolidone ("Polyplasdone XL", a product of GAF; hereinafter, simply referred to as "CLPVP") or polyvinylpyrrolidone (hereinafter, simply referred to as "PVP") (500 mg each) was added to the slightly soluble medicament EZ (500 mg), and the resultant mixture was ground while mixing with an automatic mortar at room temperature for 1 hour. A portion (50 mg; corresponding to 25 mg in terms of EZ) of each of the mixing-ground products obtained was subjected to the same procedure as Example 6 to determine the EZ content of each of the products. The wavelength employed in the determination process was 290 nm. The results are shown in FIG. 4.

COMPARATIVE EXAMPLE 6

The same procedure as Example 6 was repeated, except that EZ alone (25 mg) was used in place of the mixing-ground product (50 mg; corresponding to 25 mg in terms of EZ) to determine the EZ content of the product. The results are shown in Table 4.

INDUSTRIAL APPLICABILITY

The controlled-release preparation of the present invention in which a slightly soluble medicament is carried on the secondary particles each comprising an aggregate of spherical multivalent metal alginate microparticles is a new slightly soluble medicament-carried preparation which has not been known previously, and the manner to carry the medicament of the preparation is also new.

As is evident from Examples and Comparative Examples described above, the aggregates of the spherical calcium alginate microparticles of the present invention can remarkably improve the dissolution properties of the slightly soluble medicament and, therefore, can provide a controlled-release preparation excellent in bioavailability.

Since the aggregates of the calcium alginate microparticles have an effect to rapidly release the slightly soluble medicament carried thereon in the second solution, it is expected that the aggregates provides a rapid action of the medicament.

The spherical microparticle aggregate, which is a secondary particle of calcium alginate microparticles, can rapidly release a slightly soluble medicament carried thereon in the second solution at an dissolution rate of 99% or more. Therefore, the aggregate is less wasteful of the medicament and highly safe upon designing pharmaceuticals that should maintain the medicament in an effective blood level when administered to a subject.

After the medicament is released out of the calcium alginate microparticles in the second solution completely, the calcium alginate is converted into sodium alginate by the ion exchange between the calcium ions of the calcium alginate and the sodium ions of an aqueous sodium chloride solution and the like, and changes its nature to water-soluble and finally absorbed to or eliminated from a body. From this reason, the secondary particle which comprises a spherical aggregate of calcium alginate microparticles is suitable as a carrier for a medicament.

The calcium alginate beads with a slightly soluble medicament carried thereon have such a desirable property that the medicament is released in the stomach in a small amount, released sustainedly in the upper part of the small intestine and released in the intestine in a large amount. Accordingly, it also becomes possible to formulate enteric preparations which can release a slightly soluble medicament not in the stomach but in the intestine by the process comprising granulating calcium alginate beads with the medicament carried thereon, formulating the medicament-carried calcium alginate beads into the form of granules, tablets, capsules and the like, and then coating the formulations with an enteric coating such as CMC (carboxymethyl cellulose).

Accordingly, it becomes possible to impart such an unprecedented property that the medicament is completely released in the intestine to the controlled-release preparations with a medicament such as indomethacin and ethenzamide.

The controlled-release preparation of the present invention can be produced in a short time in a dry system. Therefore, the preparation is desirable in the viewpoint of countermeasures for the reduction of manufacturing costs upon formulation, and also desirable in the viewpoint of anti-GMP measure since the reduction in the numbers of items of process validation can be attained.

What is claimed is:

1. A process for preparing aggregates of spherical microparticles of a multivalent metal alginate, which comprises the steps of:

adding an aqueous sodium alginate solution and/or an aqueous alginic acid solution to a non-aqueous solvent comprising a polyhydric alcohol fatty acid ester, and then adding an emulsifying agent to the formed mixture so as to cause emulsion dispersion, thereby forming a water-in-oil (W/O) type emulsion;

adding an aqueous solution of a multivalent metal salt to the emulsion to form spherical microparticles of the multivalent metal alginate; and spray-drying a suspension of the spherical microparticles in water, thereby forming aggregates of the spherical microparticles.

2. The process of claim 1, wherein the aggregate is a secondary particle which is an aggregate of a plurality of primary spherical microparticles having a mean particle diameter ranging from 0.01 to 5 $\mu$m inclusive, and wherein the aggregate has a specific surface area ranging from 1 to 280 $m^2/g$ inclusive.

3. The process of claim 1 or 2, wherein the polyhydric alcohol fatty acid ester is at least one compound selected from the group consisting of glycerol fatty acid esters and propylene glycol fatty acid, the constituent fatty acid of the ester having 18 or less carbon atoms and a melting temperature of 50° C. or less.

4. The process of claim 1 or 2, wherein the emulsifying agent is at least one compound selected from the group consisting of sorbitan fatty acid esters, polyglycerol fatty acid esters and poly(rycinoleic acid) polyglycerol esters.

5. The process of claim 1 or 2, wherein the multivalent metal is at least one metal having a valency of 2 or more selected from the group consisting of calcium, zinc, beryllium, copper, barium, cadmium, strontium, radium, iron, aluminum, cobalt, nickel, chromium and manganese.

6. The process of claim 1 or 2, wherein the multivalent metal is calcium.

7. The process of claim 1, wherein the polyhydric alcohol fatty acid ester comprises a fatty acid constituent of 18 or less of carbon atoms and a melting temperature of 50° C. or less.

8. The process of claim 1, wherein the polyhydric alcohol fatty acid ester comprises a fatty acid glyceride.

9. The process of claim 1, wherein the fatty acid glycerides comprises an oleic acid mono- or di- glyceride or a linoleic acid mono or di-glyceride.

10. The process of claim 1, wherein the polyhydric alcohol fatty acid ester comprises an organic acid monoglyceride.

11. The process of claim 10, wherein the organic acid monoglyceride comprises a citric acid, a succinic acid, a malic acid or a diacetyltartaric acid.

12. The process of claim 1, wherein the polyhydric alcohol fatty acid ester comprises a triglyceride of middle-chain fatty acid.

13. The process of claim 1, wherein the polyhydric alcohol fatty acid ester comprises a propylene glycol fatty acid ester.

14. The process of claim 13, wherein the propylene glycol fatty acid ester comprises a caprylic acid mono- or di-ester, a capronic acid mono- or di-ester.

* * * * *

UNITED STATES PATENT AND TRADEMARK OFFICE
CERTIFICATE OF CORRECTION

PATENT NO.   : 6,274,174 B1  Page 1 of 1
DATED        : August 14, 2001
INVENTOR(S)  : Takeshi Hom-Ma et al.

It is certified that error appears in the above-identified patent and that said Letters Patent is hereby corrected as shown below:

Column 8,
Line 64, please delete "5 am" and replace with -- 5 µm --.

Signed and Sealed this

Fourth Day of June, 2002

*Attest:*

*Attesting Officer*

JAMES E. ROGAN
*Director of the United States Patent and Trademark Office*